(12) United States Patent
Li et al.

(10) Patent No.: US 9,255,868 B2
(45) Date of Patent: Feb. 9, 2016

(54) WINDING TESTER FOR COMPOSITE WIRE ROD-TYPE SPECIMENS

(75) Inventors: Rui Li, Hangzhou (CN); Miao Qian, Hangzhou (CN); Minbo Yu, Hangzhou (CN); Guoyong Li, Hangzhou (CN); Zhihua Zhu, Hangzhou (CN); Hongyun Yu, Hangzhou (CN); Qun Yuan, Hangzhou (CN)

(73) Assignee: Zhejiang Huadian Equipment Testing Institute, Hangzhou, Zhejiang (CN)

( * ) Notice: Subject to any disclaimer, the term of this patent is extended or adjusted under 35 U.S.C. 154(b) by 236 days.

(21) Appl. No.: 13/979,829

(22) PCT Filed: May 3, 2012

(86) PCT No.: PCT/CN2012/075011
§ 371 (c)(1),
(2), (4) Date: Jul. 15, 2013

(87) PCT Pub. No.: WO2013/007127
PCT Pub. Date: Jan. 17, 2013

(65) Prior Publication Data
US 2013/0291648 A1 Nov. 7, 2013

(30) Foreign Application Priority Data
Jul. 12, 2011 (CN) .......................... 2011 1 0194600

(51) Int. Cl.
*G01F 15/14* (2006.01)
*G01N 3/26* (2006.01)
(Continued)

(52) U.S. Cl.
CPC .. *G01N 3/26* (2013.01); *G01N 3/20* (2013.01); *G01N 3/28* (2013.01); *G01N 2203/028* (2013.01); *G01N 2203/0264* (2013.01)

(58) Field of Classification Search
CPC ............. G01N 3/26; G01N 3/22; G01N 3/08; B64G 1/56; E21B 45/00; G01V 11/00
USPC .............. 73/432.1, 847, 152.45, 829, 564.08, 73/587, 152.04, 152.17, 152.44, 152.46, 73/152.52, 808, 811, 814; 702/6
See application file for complete search history.

(56) References Cited

U.S. PATENT DOCUMENTS 5,826,654 A * 10/1998 Adnan .................... E21B 19/22
166/250.01
5,992,248 A * 11/1999 Gottfert ................... G01N 3/08
425/324.1

(Continued)

FOREIGN PATENT DOCUMENTS

CN 101706399 A 5/2010
CN 102353597 A 2/2012

(Continued)

*Primary Examiner* — Lisa Caputo
*Assistant Examiner* — Nigel Plumb
(74) *Attorney, Agent, or Firm* — Muncy, Geissler, Olds & Lowe, P.C.

(57) ABSTRACT

It is provided a dedicated winding tester for composite wire rod-type specimens for effectively measuring the minimum winding radius of the wire rod-type specimens being made with carbon fiber or glass fiber reinforced composites in various diameters or textures via automatically gripping specimens, tightly winding, and sequentially proceeding sustained load in time, thereby supplying test data and design consideration in actual use and transport of the wire rod-type specimens being made of carbon fiber or glass fiber reinforced composites that comprises a shield, a specimen receiver and a winding device being arranged within said shield, as well as a programmable controller being arranged outside the shield.

10 Claims, 20 Drawing Sheets

(51) Int. Cl.
*G01N 3/20* (2006.01)
*G01N 3/28* (2006.01)

(56) References Cited

U.S. PATENT DOCUMENTS

| | | | | |
|---|---|---|---|---|
| 6,321,596 | B1 * | 11/2001 | Newman | E21B 19/22 73/152.45 |
| 7,444,861 | B2 * | 11/2008 | De Jesus | E21B 19/22 73/152.59 |
| 7,458,267 | B2 * | 12/2008 | McCoy | G01N 29/14 166/384 |
| 7,536,911 | B2 * | 5/2009 | Kim | G01M 5/0033 250/227.18 |
| 7,577,552 | B2 * | 8/2009 | Sugihara | G06F 17/5009 703/1 |
| 2002/0069675 | A1 * | 6/2002 | Bumgarner | B65H 54/88 65/378 |

FOREIGN PATENT DOCUMENTS

| | | |
|---|---|---|
| CN | 202158998 U | 3/2012 |
| SU | 1193512 A | 11/1985 |

* cited by examiner

WINDING TESTER FOR COMPOSITE WIRE ROD-TYPE SPECIMENS

TECHNICAL FIELD

The present invention generally relates to test apparatus for wire-type material used for power transmission line, in particular, relates to a winding tester for the wire rod-type specimens with carbon fiber or glass fiber reinforced composites, specifically provides for a winding tester with carbon fiber or glass fiber reinforced composite wire rod-type specimens.

BACKGROUND

Carbon fiber or glass fiber resin is a composite material being made with carbon fiber or glass fiber as reinforcing phase mingled in a resin as matrix phase. It meets the requirements to wire core material of the novel power transmission line in power industry, because of a series of outstanding performance thereof, such as, high specific strength, high specific modulus, high temperature resistance, corrosion resistance, fatigue resistance, and creep resistance, as well as small sag and thermal expansion coefficient, thereby gradually emerging a new configuration of carbon fiber composite core with the center layer of carbon fiber or resin and the coating layer of glass fiber or resin, as time required. It is found that, in subsequent studies, compared with conventional a steel core, the quality and linear expansion coefficient of the carbon fiber or glass fiber composite core equals approximately to $1/5$ and $1/12$ thereof, respectively. The outer layer, namely coating layer of glass fiber reinforces the wear resistance of the wire rod-type specimens, and is conducive to alleviate the damage generated between the wire rod-type specimens and an aluminum wire. The smooth surface of the wire rod-type specimens enables mating it directly with soft aluminum wire with trapezoidal cross section without processing, that is available for possibility and necessity of its application in transmission overhead line industry, further decrease of the power consumption during transmission, and reduction of 20% quantities of tower rods for land saving, as well as reduction of the metal resource consumption, thus contributing to the implementation of a power grid with environmental protection and power saving of high efficiency.

In order to facilitating the transport and discharge of transmission wire, generally winding its core composite around a disk of reasonable size. For more delivery quantities of wire, it is usually chosen that winding the core composite around the disk in a size as small as possible. However, carbon fiber or glass fiber composite core is configured with high elastic modulus and low elongation that the outer layer of its glass fiber being exposed is prone to cause the exposed surface defects where scratches or damages is not to be promptly detected, the use of the undersized disk may in turn lead to make the wire rod-type specimens damaged or even broken.

There is a need, therefore, for how to quickly and effectively estimate the exposed surface defects of the carbon fiber or glass fiber composite core, and to provide a safe and reasonable radius of curvature for the transport and discharge of the carbon fiber or glass fiber composite core line. A need exists for the primary issue as aforementioned that promotes safe operation of transmission line in new power industry.

SUMMARY

The present invention fulfills the above needs and addresses or alleviates the aforementioned detects in prior art, as well as others, by providing a dedicated winding tester for composite wire rod-type specimens for effectively measuring the minimum winding radius of the wire rod-type specimens being made with carbon fiber or glass fiber reinforced composites in various diameters or textures via automatically gripping specimens, tightly winding, and sequentially proceeding sustained load in time, thereby supplying test data and design consideration in actual use and transport of the wire rod-type specimens being made of carbon fiber or glass fiber reinforced composites.

In one feature of the present invention, the winding tester for composite wire rod-type specimens comprising a shield, a specimen receiver and a winding device being arranged within said shield, as well as a programmable controller being arranged outside the shield, which is characterized in that the specimen receiver includes a pair of stand seats and a pair of guide mechanisms disposed in front and rear portions between the two stand seats, respectively, each of which includes a bearing, a hand wheel, a polish rod, a pressing plate and a pair of upper guide pulleys and a pair of lower guide pulleys oppositely arranged, wherein the hand wheel passes through the top plate of the bearing and then mates with the pressing plate in screw joint; a rotating spindle of the upper guide pulley is arranged between the two pressing plates with which two ends being penetrated respectively into two vertical grooves set in lateral plates of the bearing; a rotating spindle of the lower guide pulley is arranged between the two lateral plates of the bearing; the polish rod is shafted and connected into the lateral plates of the bearing with which two ends being fixed respectively onto the pair of stand seats, as the polish rod being in parallel with the rotating spindle of the upper guide pulley and the rotating spindle of the lower guide pulley.

the winding device includes a support frame, a drive motor, a winding wheel and a clamp, wherein the drive motor is arranged onto the support frame with which extended end being disposed of a linkage driving shaft on which the winding wheel being disposed; the clamp includes a connector, on which an accommodating slot being formed, being disposed on the winding wheel, a wire rod-type specimens gripping sleeve, on which sleeve bulge a wire rod-type specimens hole being set on one side of the connector, a gasket and a bolt, wherein the sleeve body of the wire rod-type specimens gripping sleeve is disposed within the accommodating slot, the sleeve tail of the wire rod-type specimens gripping sleeve is set with a screw hole, the gasket and the bolt are arranged on the other side of the connector, the bolt mates with the screw hole of the wire rod-type specimens gripping sleeve.

In a preferred embodiment of the winding tester for composite wire rod-type specimens, it features that 1. The specimen receiver enables smoothly feeding the wire-type specimens, whereon the tension maintaining contact, along a predetermined orientation, that the radius of curvature of the specimen equals to the outer diameter of the winding wheel, thereby guaranteeing the accuracy and reliability of the testing process.

2. The advantageous aspects, for example, simplified configuration, eased operation, and automatic feeding, of the winding device of the preferred embodiment in the present invention enables which widely being used for various types of specimens by, such as, regulating the motor speed or the outer diameter of the winding wheel thereof as needed.

3. The preferred embodiment of the winding tester is configured with a programmable controller which can automatically set and control the winding test for various types of the specimens, further calculate and output the test data.

The operating process of the specimen receiver of the preferred embodiment in the present invention features as following that firstly unscrewing to loosen the hand wheels of the front and rear guide mechanisms, and secondly traversing the wire-type specimen out of the space between the upper and lower guide wheels of the front guide mechanism after traversing it into the space between the upper and lower guide wheels of the rear guide mechanism, and then screwing to tighten the hand wheels of the front and rear guide mechanism, thereby clamping the specimen which maintaining a certain tension between the upper and lower guide wheels by pressing the pressing plate down. Proceeding to pull and fix the end of the specimen to the winding device. In winding test process, the specimen may travel between the upper and lower guide wheels, which in turn can be smoothly fed along the determined orientation. As the bearing can rotate around the polish rod, the feeding angle or shaking of the specimen appeared in the feeding process thus can be adjusted by said guide mechanism. At the same time, owing to the pressing plate making merely rolling motion of specimen, whereon the tension maintaining contact, without sliding relative to the guide wheels, the radius of curvature of the specimen equals to the outer diameter of the winding wheel, thereby guaranteeing the accuracy and reliability of the testing process.

In a preferred embodiment of the present invention, the polish rod of the specimen receiver is shafted and connected into the bearing through a ball bearing.

In another preferred embodiment of the present invention, on each stand seat a set of regulating holes vertically arranged are correspondingly set to fasten said polish rod of the rear guide mechanism. Due to the winding tester correspondingly configuring various types of the winding wheel in different diameter according to alternative specifications, it is needed that adjusting the height of the rear guide mechanism for ensuring tangentially pitching each test specimen in the winding wheel in a straight linear state. The rear guide mechanism is fastened to a position at the same height as the front guide mechanism thereof, for feeding the specimen in a horizontal state, where the height of the pitching-in point of the specimen on the winding wheel with a small diameter equals to the feeding height of the front guide mechanism. The rear guide mechanism is fastened into a regulating hole at an upper height than the front guide mechanism thereof, for feeding the specimen in a horizontal state, where the height of the pitching-in point of the specimen on the winding wheel with a large diameter is lower than the feeding height of the front guide mechanism. The regulating hole as mentioned above is disposed according to the individual diameter of winding wheel.

In still another preferred embodiment of the present invention, on each stand seat a vertical guide groove communicated with each regulating hole is further set. It is implemented for a simplified operation that turning the polish rod into a new regulating hole as long as turning it out of the prior hole and moving it into the vertical guide groove among changing the winding wheel with alternative diameter.

In yet another preferred embodiment of the present invention, on each stand seat a vertical regulating groove is set for fastening the polish rod to the rear guide mechanism, which configuration enables steplessly regulating the height of the rear guide mechanism.

The operating process of the winding device of the preferred embodiment in the present invention features as following that passing the specimen through the wire rod-type specimens bore set in the sleeve bulge of the wire rod-type specimens gripping sleeve, fastening the specimen by screwing to tighten the bolt; sequentially, activating the motor to motivate the rotation of the linkage driving shaft, as well as winding wheel for startup of test process; deactivating the motor until the winding wheel having rotated predetermined cycles, then ending the test process; finally, reviewing the surface of specimen to determine whether any flaw or fracture exists therein.

In a preferred embodiment of the present invention, the drive motor of the winding device preferably is an integrated servo motor reducer with compact configuration, or a servo motor with automatic function of control and regulation.

In another preferred embodiment of the present invention, the winding tester correspondingly is configured with various types of the winding wheels in different diameter according to alternative specifications to determine the minimum winding radius of each wire rod-type specimens. The hub of the winding wheel should have enough high intensity to support the centripetal force generated during winding of which, however, plate contacting with the wire rod-type specimens may not have too high intensity to damage the surface layer fiber of the composite wire rod-type specimens so that causes the crack thereof and then affects the test result. The weight of the hub should be small as possible to ease to change. The preferred embodiment of the invention therefore preferably is disposed of the hub with high-intensity MC nylon, and a plurality of thru hole uniformly on the disk surface of a hub of the winding wheel of the winding device without affecting the intensity of the hub, thereby still reaching of ease to change.

In still another preferred embodiment of the present invention, an anti-delinking cap is disposed at the outer periphery of the linkage driving shaft, for preventing the winding wheel falling out during the winding process.

In yet another preferred embodiment of the present invention, a displacement encoder is further on the linkage driving shaft, for transforming the signal representative of the rotation cycle numbers to a electrical signal and outputting the signal to the programmable controller to be calculated, and loading for 30 seconds after reaching of a predetermined value until the test terminates to implement the automatic control of the process.

In alternatively another preferred embodiment of the present invention as shown in FIG. 3, the two lateral plates 201 of the shield are provided with a bi-layer configuration with an inner layer 202 of metal punching screen and an outer layer 203 of organic glass plate which facilitates observation by the test personnel and prevents the fracture splashing out. The top plate of the shield is a detachable metal plate. At the front of the shield two visual gates, which are provided with material of bi-layer colorless toughened glass with receiving by seal glue therebetween, are arranged for reinforcing the shock resistance of the glass.

In alternatively another preferred embodiment of the present invention, a visual monitoring system is further arranged on the shield, which comprises a monitor disposed outside the shield, a monitor distribution box disposed above the shield, which supplies electric power for said visual monitoring system and stores a recorder for repeating the display, and cameras disposed at four inner corners within the shield which enables visually monitoring the test process, and aligned with the disk surface of the hub of the tester which enables capturing the surface state of the specimen in its circumference direction from four individual directions and visually representing on a display, thereby covering entire winding surface of the specimen. The configuration and operation ensure the test personnel to be safe, but also achieve the real time monitoring and recording of the test process, which in turn enhance the reliability of determination to the damage situation of the specimen.

BRIEF DESCRIPTION OF THE ACCOMPANYING DRAWINGS

wherein, elements are not to scale so as to more clearly show the details, wherein the like reference numbers indicate like elements throughout the several views, and wherein:
1—wire-type specimens, 2—shield, 3—winding device, 4—visual gate, 5—specimen receiver, 6—programmable controller, 7—monitor, 8—camera, 9—monitor distribution box;
501—regulating hole, 502—front guide mechanism, 503—rear guide mechanism, 504—bracing plate, 505—stand seat, 506—hand wheel, 507—polish rod, 508—anti-delinking cap, 509—ball bearing, 510—lower guide wheel, 511—pressing plate, 512—bearing, 513—upper guide wheel, 514—top plate, 515—lateral plate, 516—upper rotating spindle, 517—vertical groove, 518—lower rotating spindle, 519—vertical guide groove, 520—vertical regulating groove, 523—specimens pitching-in point;
302—winding wheel, 303—clamp, 304—drive motor, 305—support frame, 306—anti-delinking cap, 307—displacement encoder, 308—linkage driving shaft, 309—rim, 310—key slot, 311—hub, 312—thru hole, 313—shaft sleeve, 314—mounting hole, 315—connector, 316—mounting hole, 317—wire rod-type specimens gripping sleeve, 318—wire rod-type specimens hole, 319—screw hole, 320—accommodating slot, 321—bolt, 322—gasket, 323—key slot, 324—sleeve bulge, 325—sleeve body;
601—human-person interface, 602—jerk button, 603—rubber margin foot, 604—elongated hole.

DETAILED DESCRIPTION OF THE PREFERRED EMBODIMENT

Figure 1:
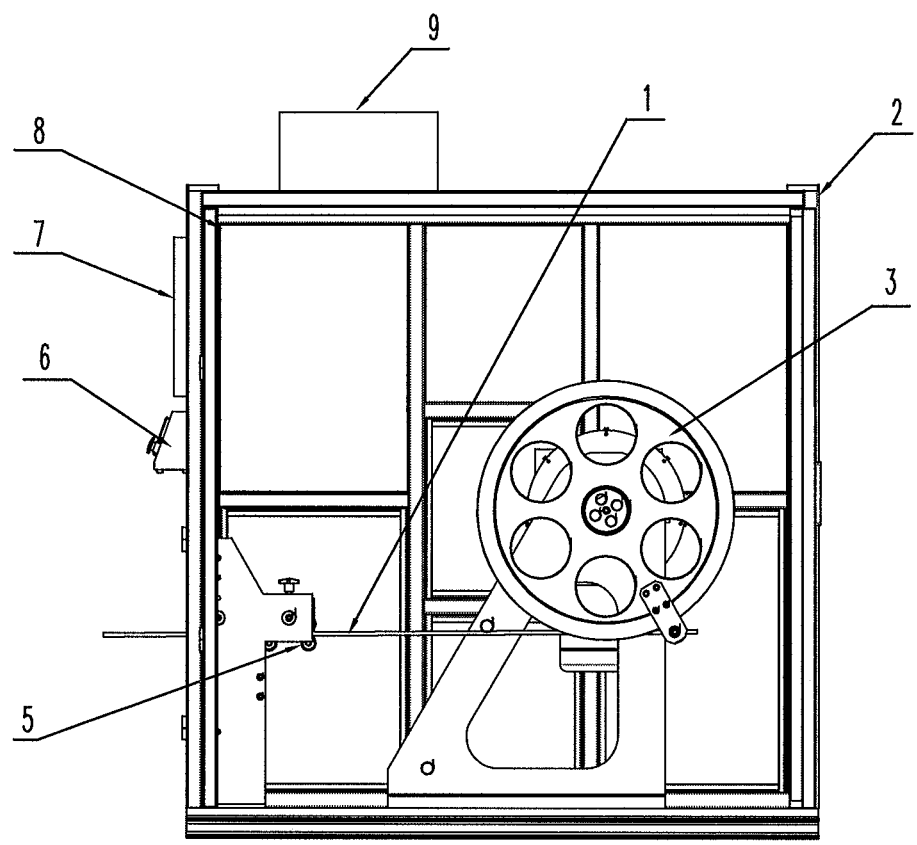
FIG. 1 shows a structural schematic diagram of the winding tester for composite wire rod-type specimens of the present invention.
Figure 2:
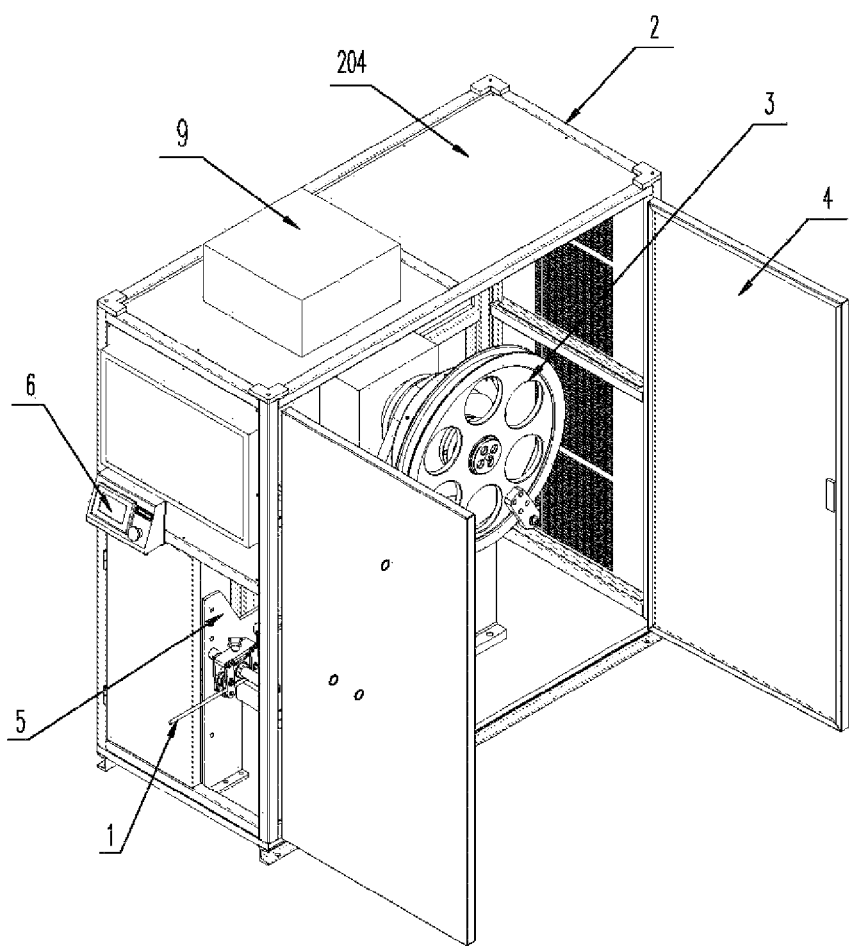
FIG. 2 shows a schematically axonometric diagram of the winding tester for composite wire rod-type specimens of the present invention.
Figure 3:
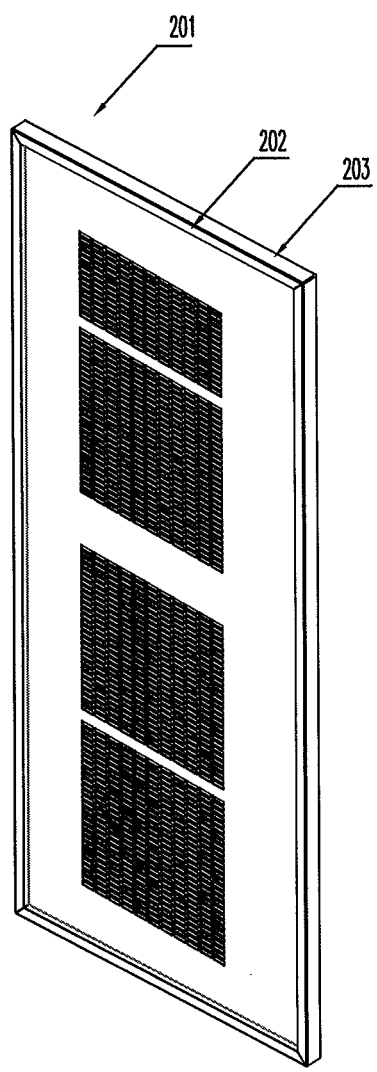
FIG. 3 shows a structural schematic diagram of the each lateral plate of the shield of the present invention.

With reference now to FIGS. 1 and 2, a preferred embodiment of the winding tester for composite wire rod-type specimens of the invention comprises a shield 2, a specimen receiver 5, and a winding device 3 being arranged within said shield 2, as well as a programmable controller 6 being arranged outside the shield 2.

Due to the splash of fiber bundle or fine dust ejected from the composite wire rod-type specimens in the moment of fracture therein, a visual monitoring system is arranged on the shield for protecting the test personnel from injury or inhalation caused by the fracture and for momentarily observing the specimen, which comprises a monitor 7 disposed outside the shield, a monitor distribution box 9 disposed above the shield, which supplies electric power for said visual monitoring system and stores a recorder for repeating the display, and cameras 8 disposed at four inner corners within the shield which enables visually monitoring the test process, and aligned with the disk surface of the hub of the tester which enables capturing the surface state of the specimen in its circumference direction from four individual directions and visually representing on a display, thereby covering entire winding surface of the specimen. The configuration and operation ensure the test personnel to be safe, but also achieve the real time monitoring and recording of the test process, which in turn enhance the reliability of determination to the damage situation of the specimen.

With reference now to FIG. 2, the top plate 204 of the shield 2 is a removable metal plate. At the front of the shield 2 two visual gates 4, which are provided with material of bi-layer colorless toughened glass with receiving by seal glue there between, are arranged.

Figure 4:
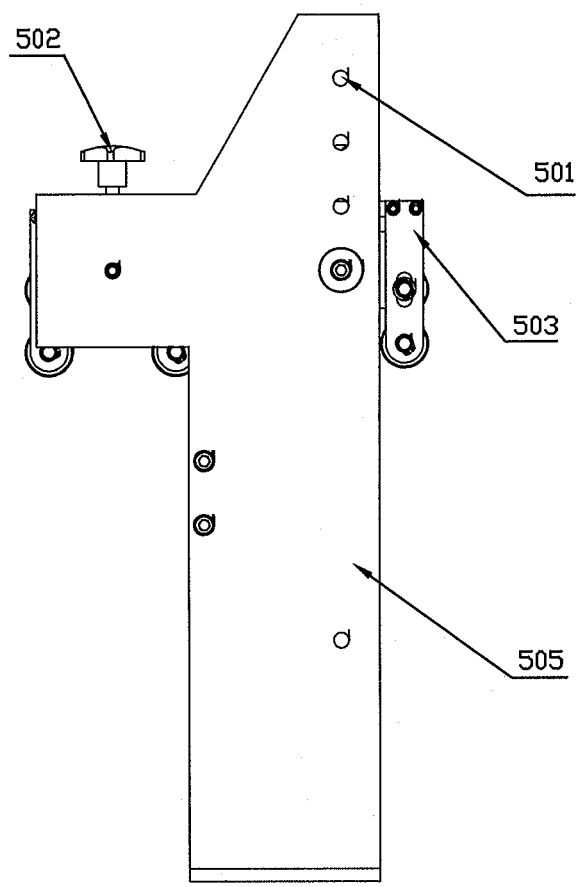
FIG. 4 shows a structural schematic diagram of the specimen receiver of the present invention.
Figure 5:
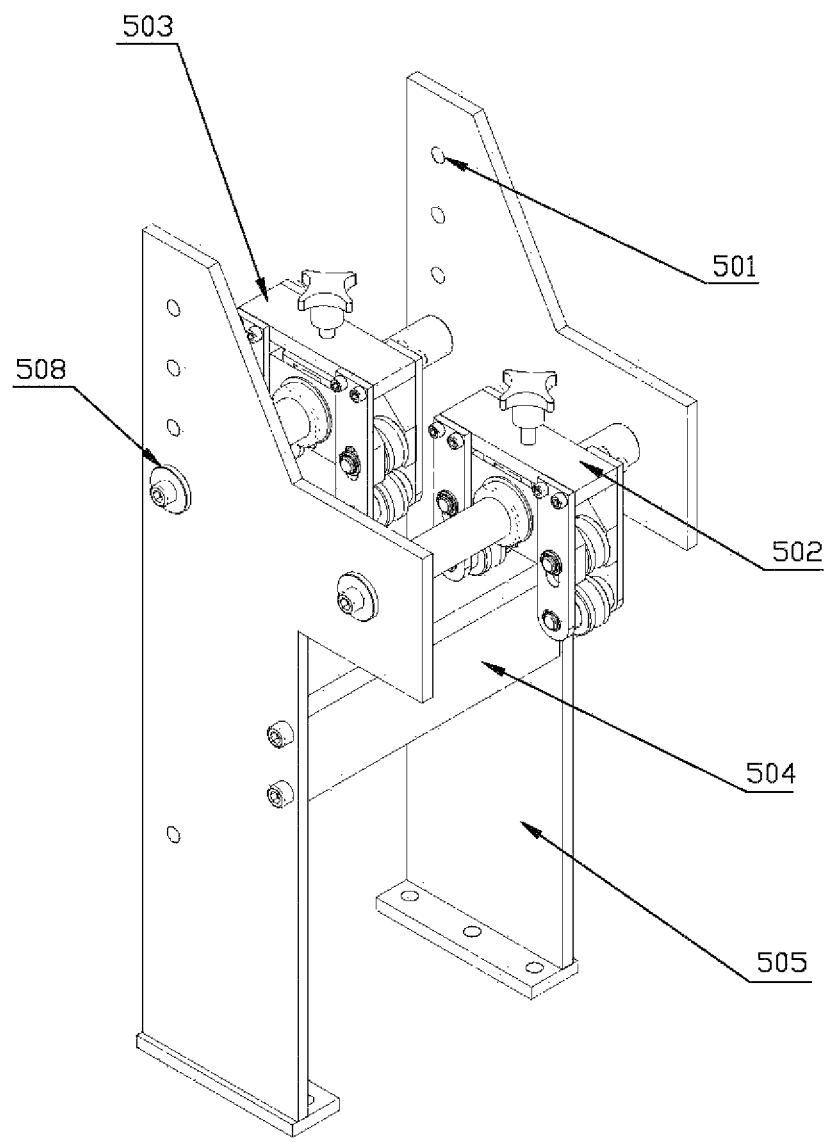
FIG. 5 shows a schematically axonometric diagram of the specimen receiver of the present invention.
Figure 6:
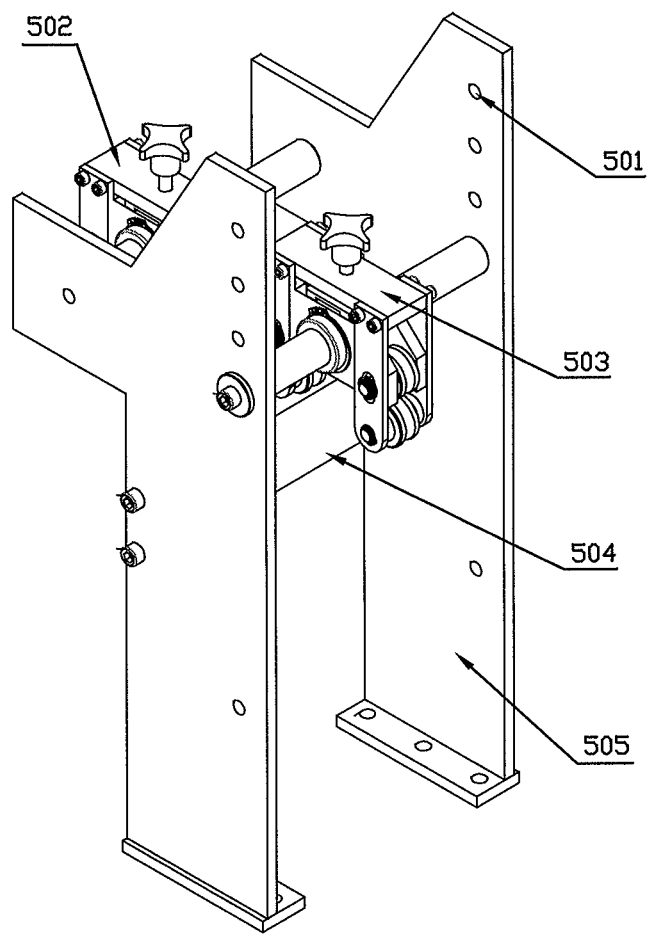
FIG. 6 shows a schematically axonometric diagram of the specimen receiver of the present invention illustrated from another viewpoint.

With reference now to FIGS. 4, 5 and 6, the specimen receiver 5 of winding tester for composite wire rod-type specimens preferably includes a pair of stand seats 505 and a pair of guide mechanism 502.503 disposed in front and rear of the stand seats 505 respectively. A bracing plate 504 is further disposed between said pair of the stand seats 505.

Figure 7:
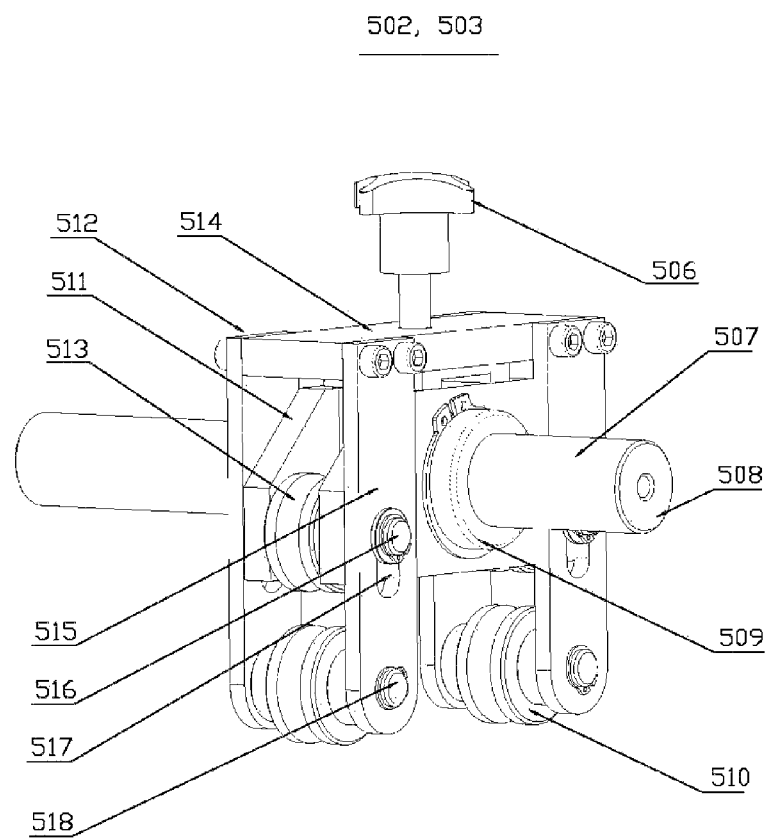
FIG. 7 shows a structural schematic diagram of a guide mechanism of the specimen receiver of the present invention.

With reference now to FIG. 7, each guide mechanism 502, 503 includes a bearing 512, a hand wheel 506, a polish rod 507, a pressing plate 511 and a pair of upper guide pulleys 513 and a pair of lower guide pulleys 510 oppositely arranged. The bearing 512 is disposed of a top plate 514 and a pair of lateral plates 515.

The hand wheel 506 disposed on the top passes through the top plate 514 of the bearing 512 and then mates with the pressing plate 511 in screw joint. An upper rotating spindle 516 of the upper guide pulley 513 is arranged onto the pressing plate 511 with which two ends being penetrated into two vertical grooves 517 set at lateral plates 515 of the bearing 512. A lower rotating spindle 518 of the lower guide pulley 510 is arranged onto lateral plates 515 of the bearing 512. The polish rod 507 is shafted and connected onto the lateral plates 515 of the bearing 512 with which two ends being fixed onto the pair of stand seats 505, as the polish rod 507 being in parallel with the upper rotating spindle 516 of the upper guide pulley 513 and the lower rotating spindle 518 of the lower guide pulley 510.

Firstly, unscrewing in a direction to loosen the hand wheels 506 of the front and rear guide mechanism, thereby moving the upper guide wheel 513 following moving the pressing plate 511, secondly, traversing the specimen 1 through the space of the upper and lower guide wheels of the front guide mechanism, and then screwing in negative direction to tighten the hand wheels 506, thereby clamping the specimen which maintaining a certain tension between the upper and lower guide wheels by pressing the pressing plate 511 down until the upper guide wheel 513 compressed the specimen.

In a preferred embodiment of the present invention, the guide wheel portion is used for guiding the carbon fiber wire rod-type specimens, as well as applying frictional resistance thereon.

In another preferred embodiment of the present invention, on each stand seat 505 a set of regulating holes 501 vertically disposed are correspondingly set to fasten said polish rod 507 of the rear guide mechanism 503.

Figure 8:
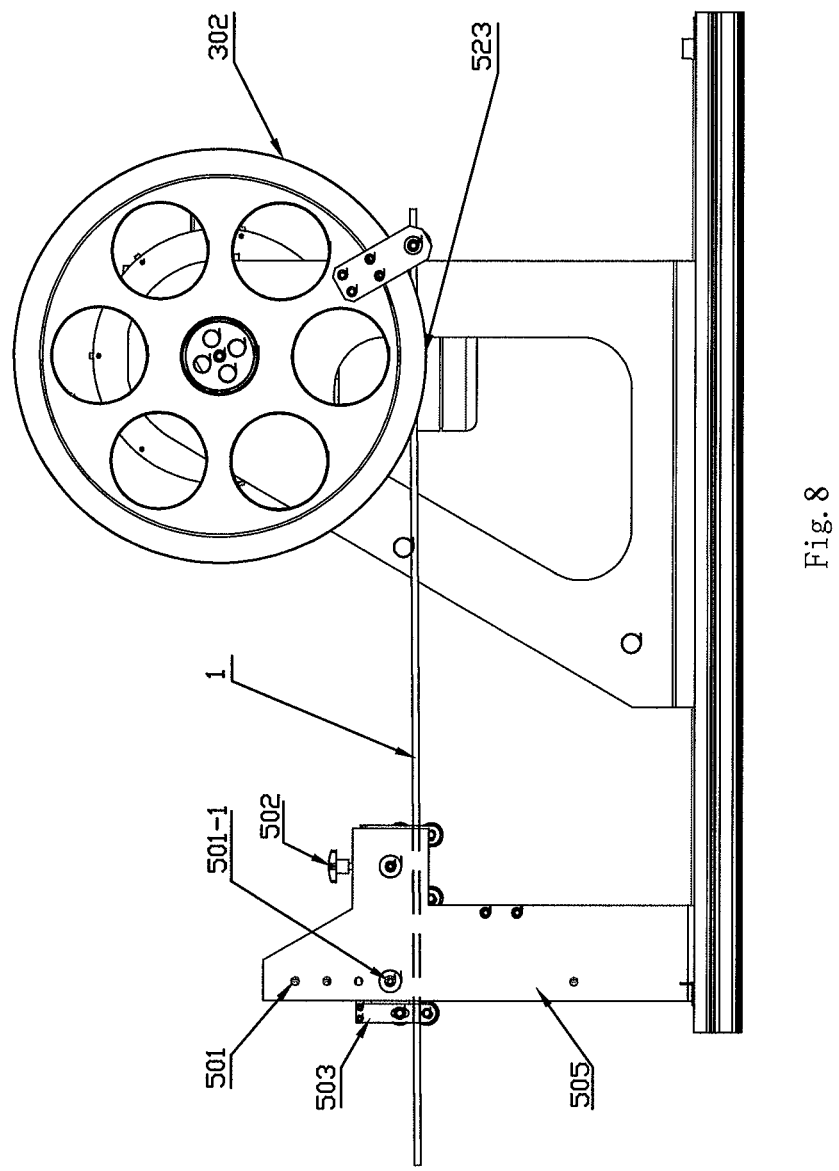
FIG. 8 shows a structural schematic diagram of the specimen receiver, disposed with a winding wheel in a small diameter, of the present invention.

With reference now to FIG. 8, due to the winding tester correspondingly configuring various types of the winding wheel in different diameter according to alternative specifications, it is needed that adjusting the height of the rear guide mechanism for ensuring tangentially pitching each test specimen in the winding wheel in a straight linear state. The rear guide mechanism 503 is fastened to a lower regulating hole 501-1 at the same height as the front guide mechanism thereof, for feeding the specimen 1 in a horizontal state, where the height of the pitching-in point 523 of the specimen on the winding wheel 302 with a small diameter equals to the feeding height of the front guide mechanism.

Figure 9:
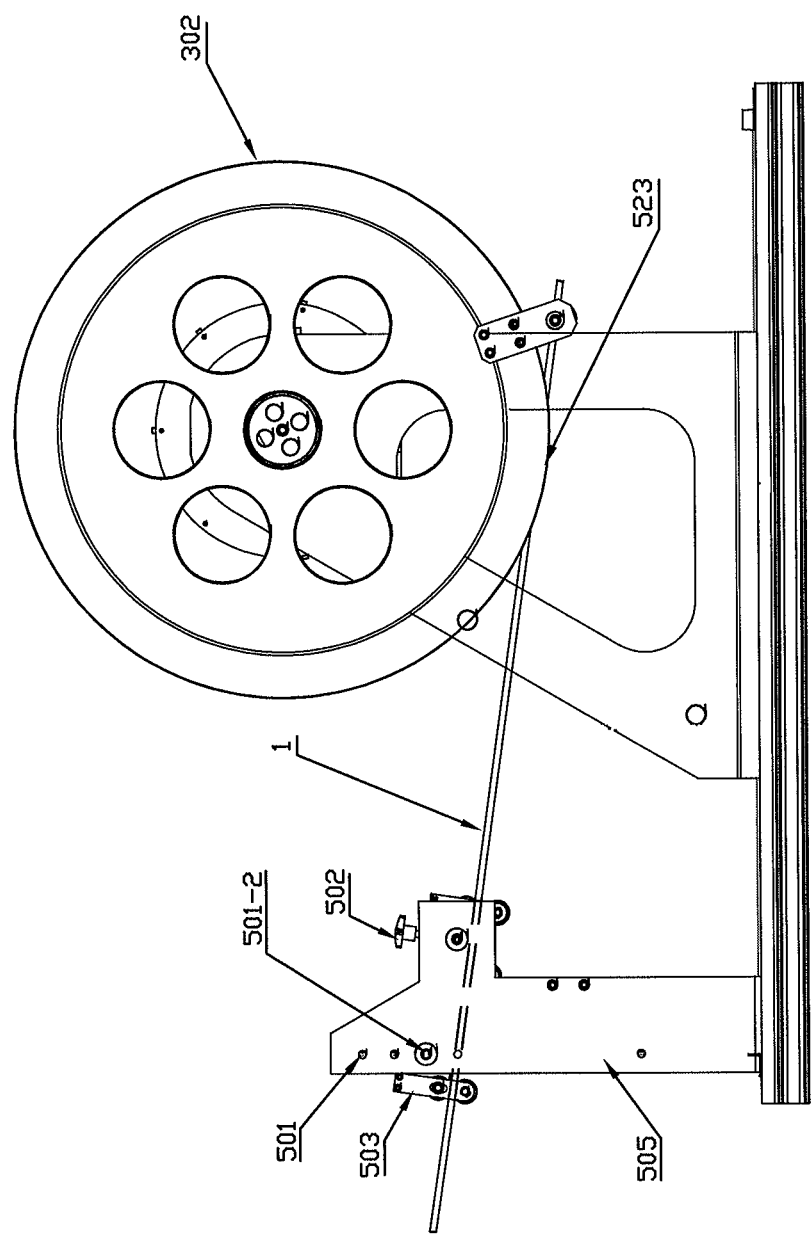
FIG. 9 shows a structural schematic diagram of the specimen receiver, disposed with a winding wheel in a large diameter, of the present invention.

With reference now to FIG. 9, the rear guide mechanism 503 is fastened into a regulating hole 501-2 at an upper height than the front guide mechanism thereof, for feeding the specimen 1 in a horizontal state, where the height of the pitching-in point 523 of the specimen on the winding wheel with a large diameter is lower than the feeding height of the front guide mechanism 502. The regulating hole as mentioned above is disposed according to the individual diameter of winding wheel.

Figure 10:
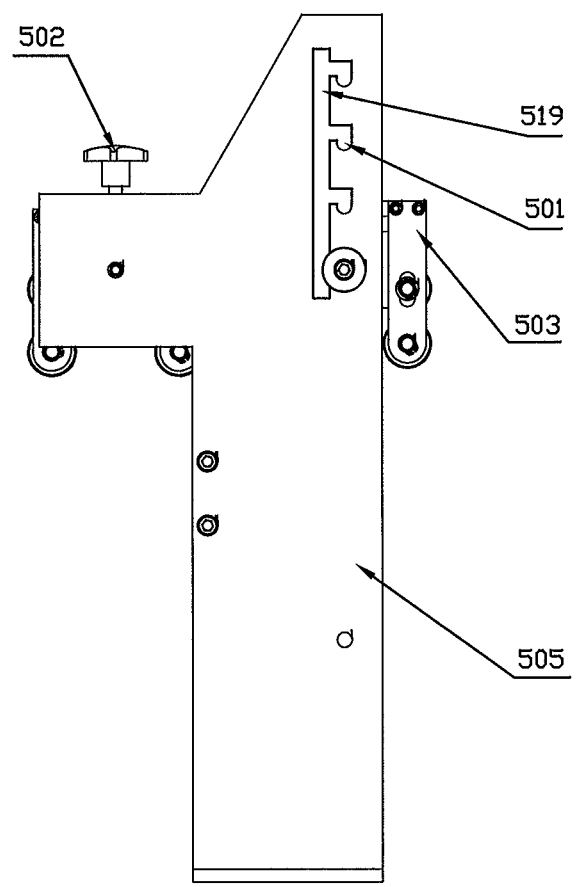
FIG. 10 shows a structural schematic diagram of a preferred embodiment of the specimen receiver, wherein disposed with vertical guide grooves, of the present invention.

In still another preferred embodiment of the present invention, with reference now to FIG. 10, on each stand seat 505 a vertical guide groove 519 communicated with each regulating hole 501 is further set. It is implemented for a simplified operation that turning the polish rod into a new regulating hole as long as turning it out of the prior holes and moving it into the vertical guide groove 519 among changing the winding wheel with alternative diameter.

Figure 11:
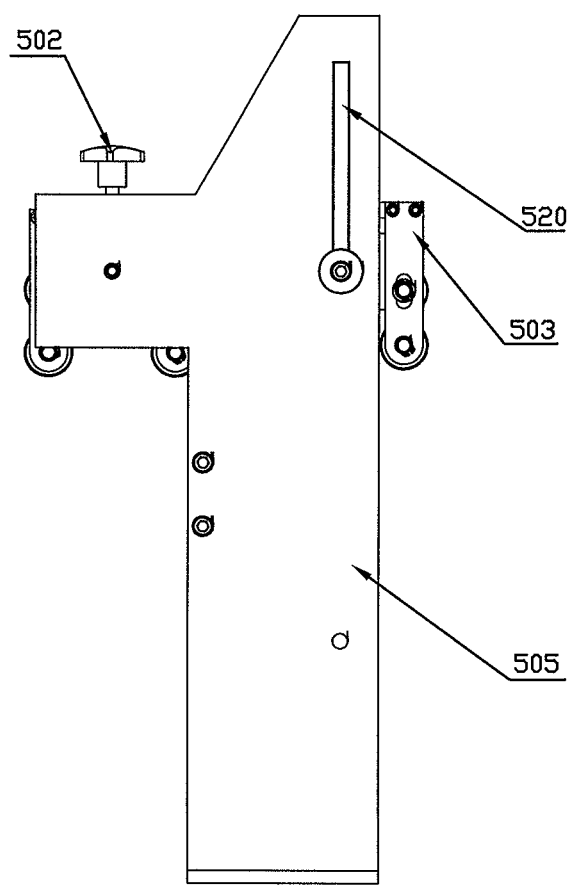
FIG. 11 shows a structural schematic diagram of a preferred embodiment of the specimen receiver, wherein disposed with vertical regulating grooves, of the present invention.

With reference now to FIG. 11, on each stand seat a vertical regulating groove 520, altering with the aforementioned regulating holes is set for fastening the polish rod to the rear guide mechanism, which configuration enables steplessly regulating the height of the rear guide mechanism 503.

In yet another preferred embodiment of the present invention, it allows that controlling the polish rod 507 via a motor-driven moving up and down manner.

Figure 12:
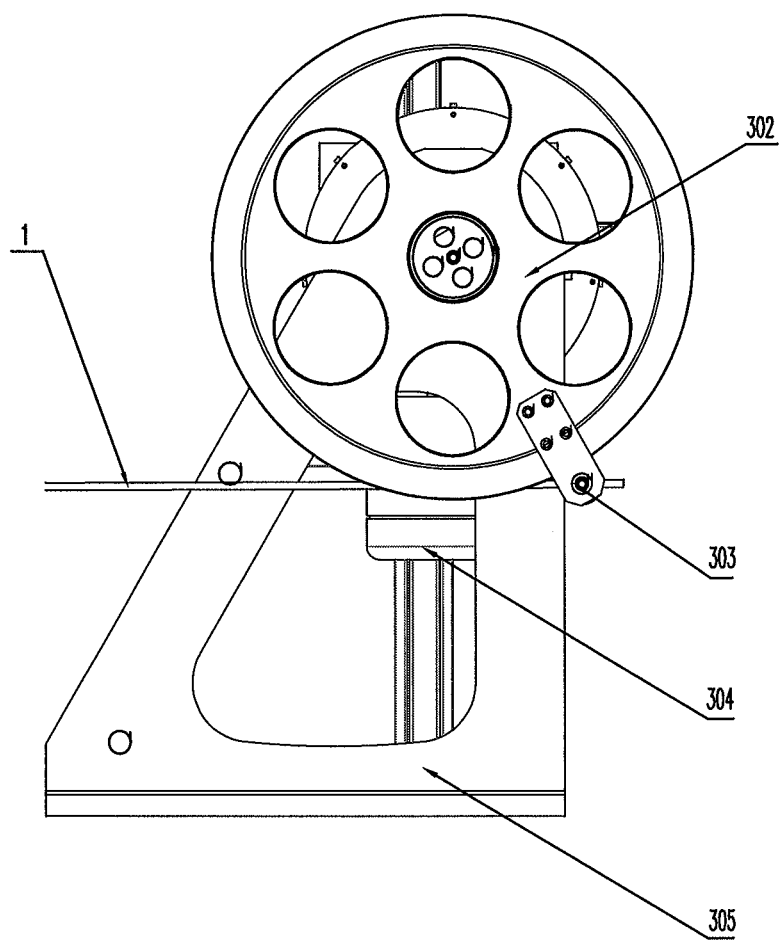
FIG. 12 shows a structural schematic diagram of a winding device of the present invention.
Figure 13:
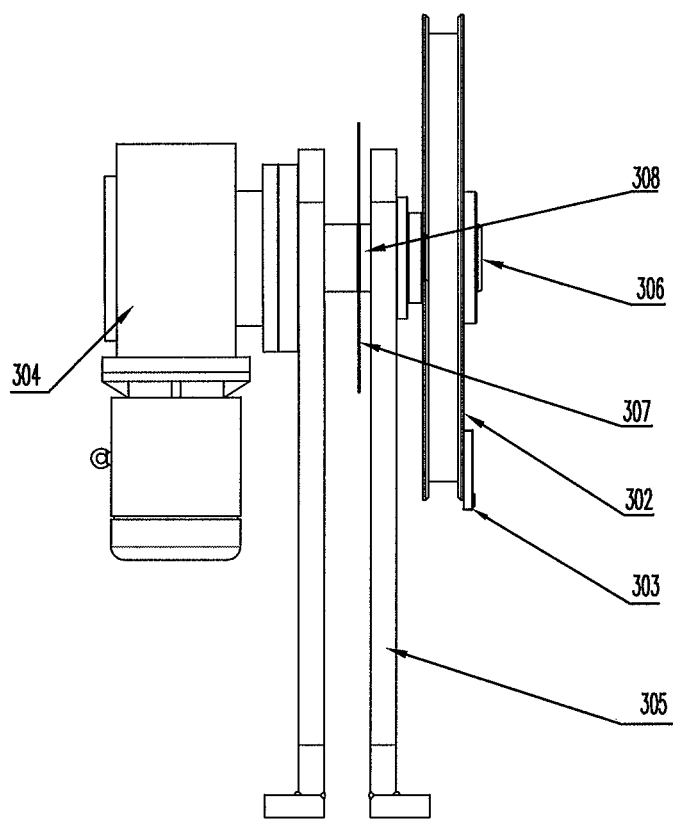
FIG. 13 shows a schematic diagram of the left view of the winding device from FIG. 12.

With reference now to FIGS. 12 and 13, a preferred embodiment of the winding device 3 of the invention preferably includes a support frame 305, a drive motor 304, a winding wheel 302 and a clamp 303, wherein the drive motor 304 is arranged onto the support 305 with which extended end being disposed of an linkage driving shaft 308 on which the winding wheel 302 being disposed. A displacement encoder 307 is further on said linkage driving shaft 308.

the clamp 303 includes a connector 315, on which an accommodating slot 320 being set, being disposed on the winding wheel 302, a wire rod-type specimens gripping sleeve 317, on which sleeve bulge 324 a wire rod-type specimens bore 318 being set on one side of the connector 315, a gasket 322 and a bolt 321, wherein the sleeve body 325 is disposed within the accommodating slot 320, the sleeve tail is set with a screw hole 319, the gasket 322 and the bolt 321 are arranged on the other side of the connector 315, the bolt 321 mates with the screw hole 319 of the wire rod-type specimens gripping sleeve 317.

Figure 14:
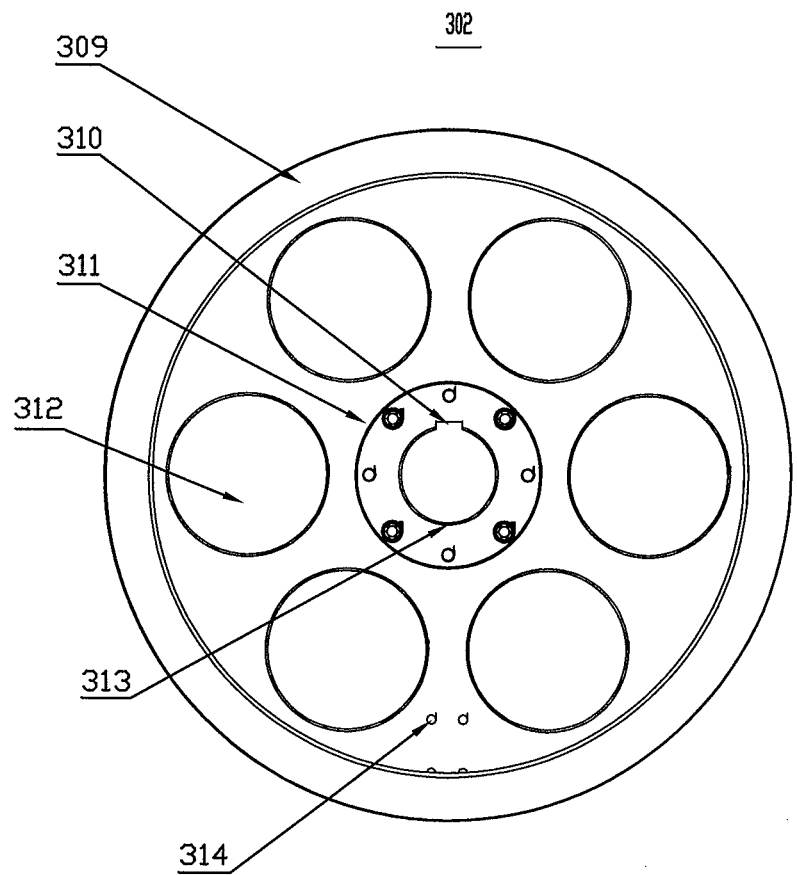
FIG. 14 shows a structural schematic diagram of a winding wheel of the winding device of the present invention.
Figure 15:
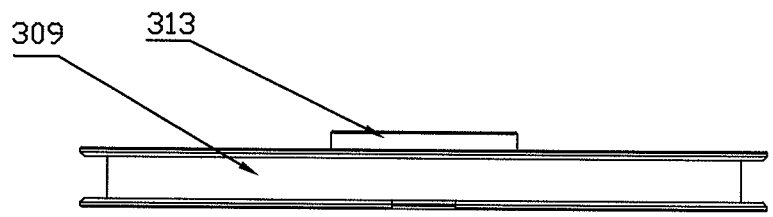
FIG. 15 shows a schematic diagram of the plan view of the winding wheel from FIG. 14 thereof.
Figure 16:
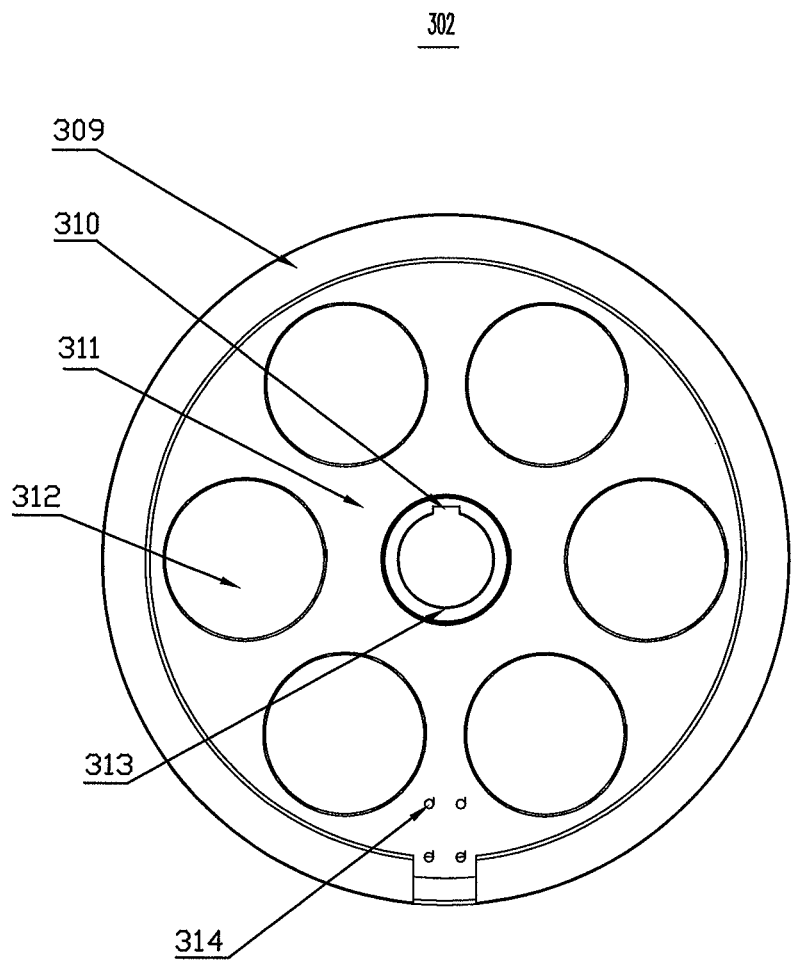
FIG. 16 shows a schematic diagram of the rear view of the winding wheel from FIG. 14 thereof.

With reference now to FIGS. 14, 15 and 16, the preferred embodiment of the winding wheel 302 preferably is disposed of the hub 311 with high-intensity MC nylon, and 306 thru hole uniformly on the disk surface of the hub of the winding wheel of the winding device without affecting the intensity of the hub, thereby still reaching of decrease the weight thereof and ease to change. Mounting holes 314 are disposed on the hub 311 for mounting the clamp 303.

Figure 17:
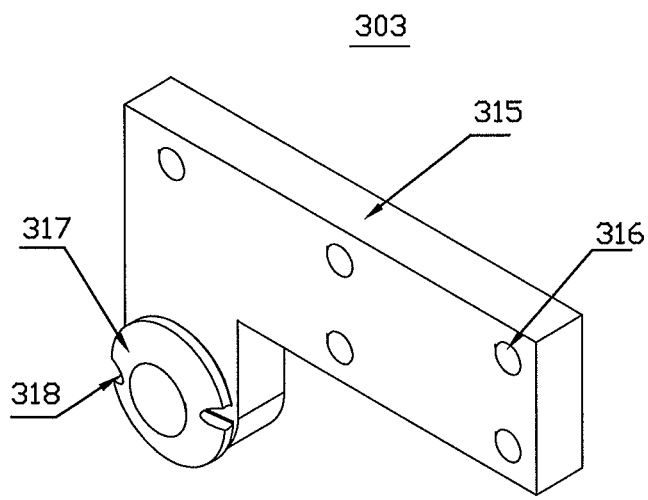
FIG. 17 shows a structural schematic diagram of a clamp of the winding device of the present invention.
Figure 18:
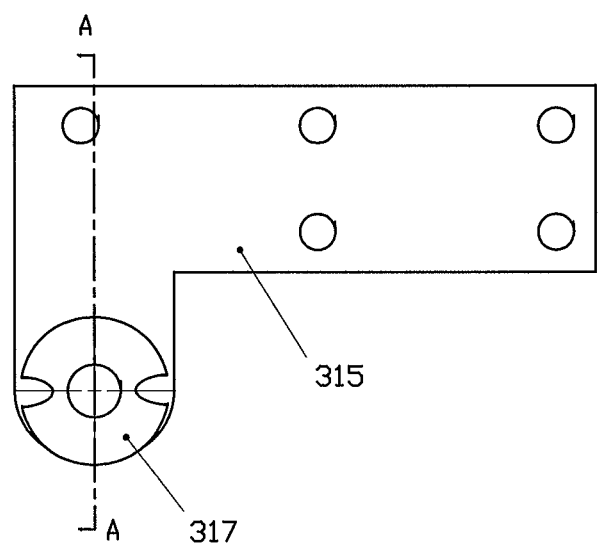
FIG. 18 shows a structural schematic diagram of a front view of the clamp.
Figure 19:
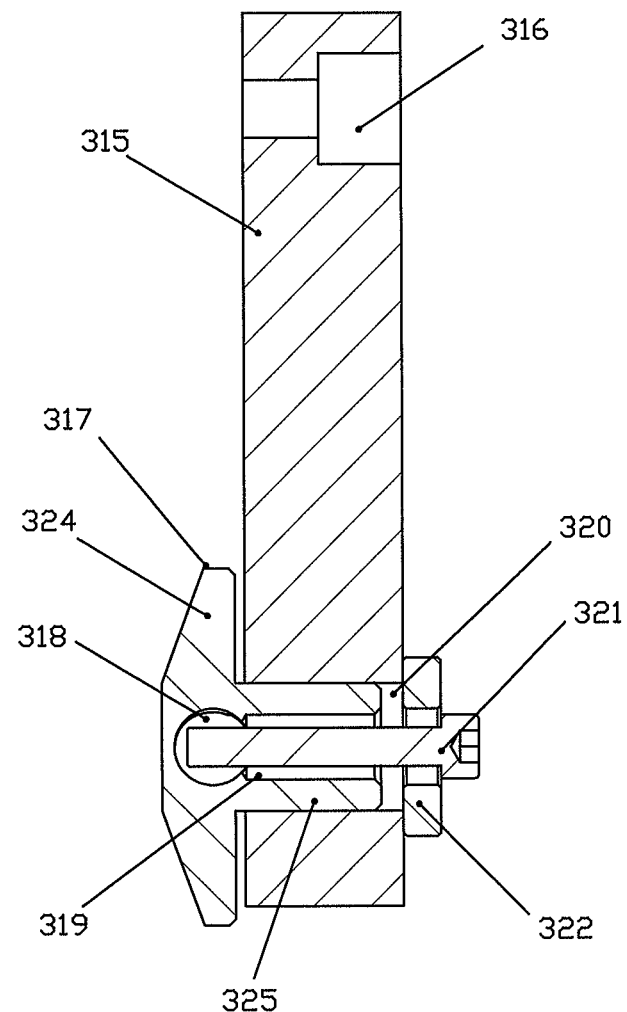
FIG. 19 shows a structural schematic diagram of an enlarged section view from A-A dash line direction of FIG. 18.

With reference now to FIGS. 17, 18 and 19, the clamp 303 includes a connector 315, on which an accommodating slot 320 being set, being disposed on the winding wheel 302, a wire rod-type specimens gripping sleeve 317, on which sleeve bulge 324 a wire rod-type specimens bore 318 being set on one side of the connector 315, a gasket 322 and a bolt 321, wherein the sleeve body 325 is disposed within the accommodating slot 320.

In still another preferred embodiment of the present invention, on the sleeve bulge 324 of the wire rod-type specimens gripping sleeve 317, a wire rod-type specimens bore 318 being set on one side of the connector 315, the sleeve tail is set with a screw hole 319, the gasket 322 and the bolt 321 are arranged on the other side of the connector 315, the bolt 321 mates with the screw hole 319 of the wire rod-type specimens gripping sleeve 317.

Passing the specimen 1 through the wire rod-type specimens bore 318 set in the sleeve bulge 324 of the wire rod-type specimens gripping sleeve, fastening the specimen by screwing to tighten the bolt 321 during the test process.

Figure 20:
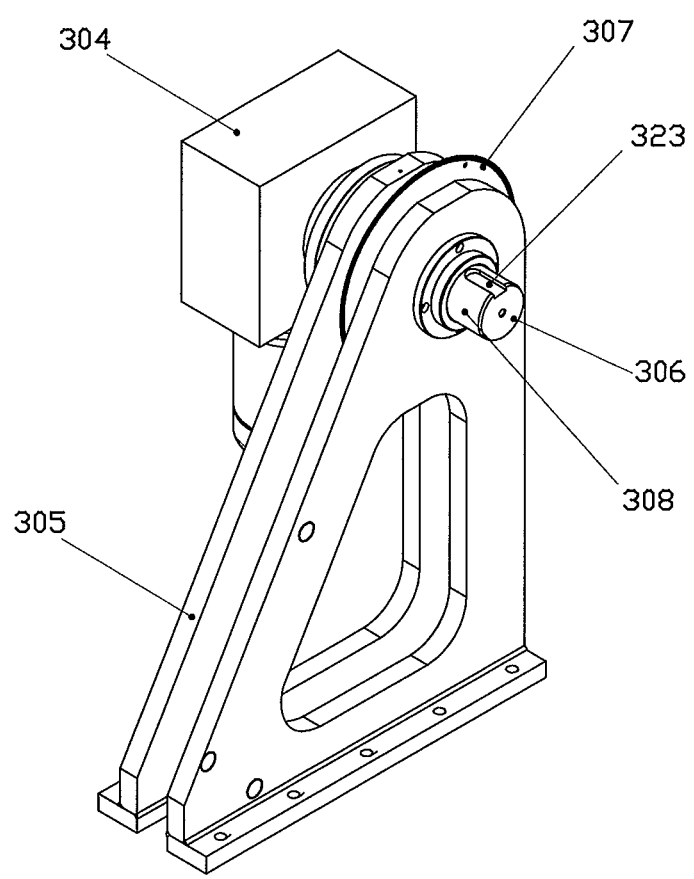
FIG. 20 shows a structural schematic diagram of an assemble and unassemble process of the winding device in the invention.

In a preferred embodiment of the present invention, as shown in FIG. 20, the winding tester correspondingly is configured with various types of the winding wheels in different diameter according to alternative specifications to determine the minimum winding radius of each wire rod-type specimens. In the change operation of the winding wheel, firstly removing of the anti-delinking cap 306, and then mounting the hub to the linkage driving shaft 308 whereon key slots 323 are set for fastening the winding wheel thereon by a keyway coupling, finally, mounting the cap 306.

In another preferred embodiment of the present invention, the diameter of the linkage driving shaft 308 is 1 mm less than the winding wheel thereof.

Figure 21:
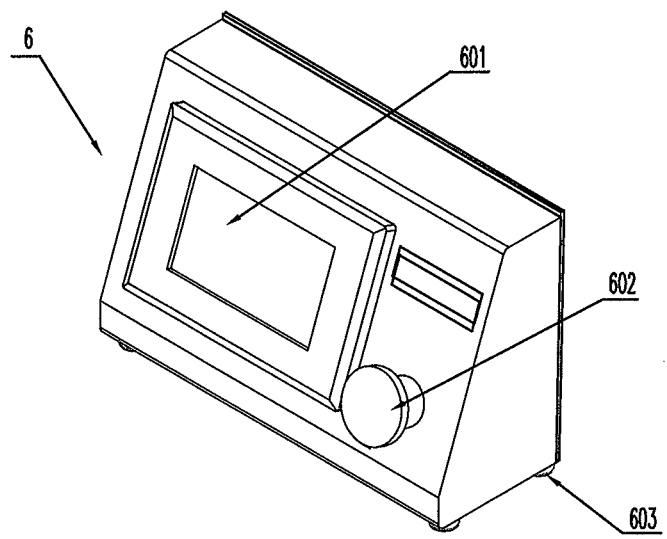
Figure 22:
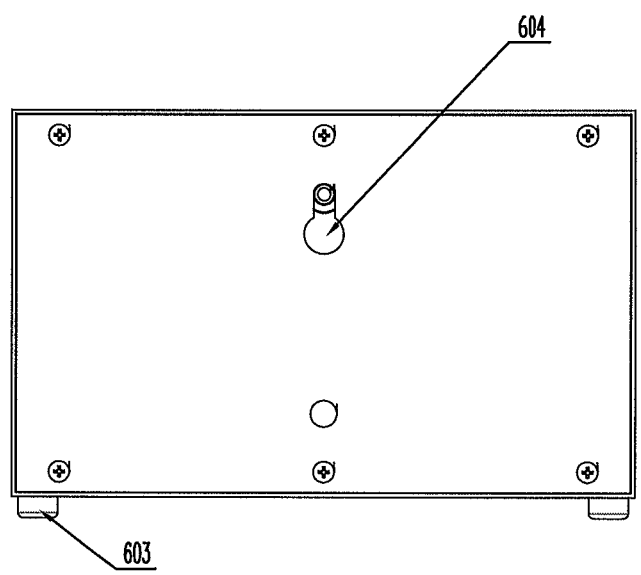
FIG. 22 shows a structural schematic diagram of a rear view of the programmable controller of the invention.

With reference now to FIGS. 21 and 22, the programmable controller 6 of the invention is preferably a pulley controller that facilitates the test personnel timely controlling the tester in any position at time of observation. At the bottom of the pulley controller, four rubber margin feet 603 are disposed, for example, for putting the controller on a desk. At the rear of the controller elongated holes 604 are set for hanging it on the shield. A jerk button 602 is further disposed on the controller for security. A human-person interface 601 is preferably disposed on the controller for setting various parameters.

Figure 23:
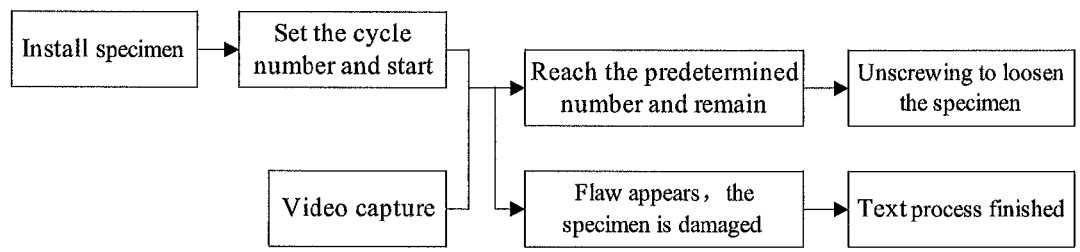
FIG. 23 shows a schematic drawing of the test process of the invention.

With reference now to FIG. 23, the operating process of the tester of the preferred embodiment in the present invention features as following that firstly activating the programmable controller 6, and then pressing the reset button for unscrewing the winding wheel 302 to the position ease to disposing of the specimen; secondly selecting the appropriate wire rod-type specimens gripping sleeve 317 corresponding to alternative specification of the carbon fiber wire rod-type specimens, traversing the wire rod-type specimens through the space of the upper and lower guide wheels of the front guide mechanism, and then penetrating it into the hole within the wire rod-type specimens gripping sleeve 317, sequentially screwing to tighten the bolt 321, thereby clamping the specimen between the upper and lower guide wheels, and then closing the gates 4 after manually screwing to tighten the hand wheels; setting winding cycle number while starting test; ending the test process until the winding wheel having rotated predetermined cycles, finally, reviewing the surface of specimen to determine whether any flaw or fracture exists therein, and then unscrewing to loosen the specimen. The test process can be repeated on a display.

It will be appreciated that the above-described embodiments are merely illustrative, and that those of ordinary skill in the art may readily devise their own implementations and modifications that incorporate the principles of the present invention and fall within the spirit and scope thereof.

What is claimed is:

1. A winding tester for composite wire rod-type specimens, comprising a shield (2), a specimen receiver (5) and a winding device (3) being arranged within said shield (2), as well as a programmable controller (6) being arranged outside the shield (2), which is characterized in that the specimen receiver (5) includes a pair of stand seats (505) and a pair of guide mechanisms (502.503) disposed in front and rear portions between said two stand seats (505), respectively, each of which includes a bearing (512), a hand wheel (506), a polish rod (507), pressing plates (511) and a pair of upper guide pulleys (513) and a pair of lower guide pulleys (510) oppositely arranged, wherein the hand wheel (506) passes through the top plate (514) of the bearing (512) and then mates with the pressing plate (511) in screw joint; an upper rotating spindle (516) of the upper guide pulley (513) is arranged between said two pressing plates (511) with which two ends being penetrated respectively into two vertical grooves (517) set in lateral plates (515) of the bearing (512); a lower rotating spindle (518) of the lower guide pulley (510) is arranged between the two lateral plates (515) of the bearing (512); the polish rod (507) is shafted and connected into the lateral plates (515) of the bearing (512) with which two ends being fixed respectively onto the pair of stand seats (505), as the polish rod (507) being in parallel with the upper rotating spindle (516) of the upper guide pulley (513) and the lower rotating spindle (518) of the lower guide pulley (510);

the winding device (3) includes a support frame (305), a drive motor (304), a winding wheel (302) and a clamp (303), wherein the drive motor (304) is arranged onto the support frame (305) with which extended end being disposed of a linkage driving shaft (308) on which the winding wheel (302) being disposed; the clamp (303) includes a connector (315), on which an accommodating slot (320) being formed, being disposed on the winding wheel (302), a wire rod-type specimens gripping sleeve (317), on which sleeve bulge (324) a wire rod-type specimens hole (318) being set on one side of the connector (315), a gasket (322) and a bolt (321), wherein the sleeve body (325) of the wire rod-type specimens gripping sleeve (317) is disposed within the accommodating slot (320), the sleeve tail of the wire rod-type specimens gripping sleeve (317) is set with a screw hole (319), the gasket (322) and the bolt (321) are arranged on the other side of the connector (315), the bolt (321) mates with the screw hole (319) of the wire rod-type specimens gripping sleeve (317).

2. The winding tester for composite wire rod-type specimens of claim 1, wherein the polish rod (507) of the specimen receiver (5) is shafted and connected into the bearing (512) through a ball bearing (509), on each stand seat (505) a set of regulating holes (501) vertically arranged are correspondingly set to fasten said polish rod (507) of the rear guide mechanism (503).

3. The winding tester for composite wire rod-type specimens of claim 2, wherein on said each stand seat (505) a vertical guide groove (519) communicated with each regulating hole (501) is further set.

4. The winding tester for composite wire rod-type specimens of claim 1, wherein the drive motor (304) of the winding device (3) is an integrated servo motor reducer.

5. The winding tester for composite wire rod-type specimens of claim 1, wherein on the disk surface of a hub (311) of the winding wheel (302) of the winding device (3), a plurality of thru holes (312) are uniformly set.

6. The winding tester for composite wire rod-type specimens of claim 1, wherein on the winding wheel (302) of the winding device (3) a shaft sleeve (313) mating with the linkage driving shaft (308) in keyway coupling is disposed, an anti-delinking cap (306) is disposed at the outer periphery of the linkage driving shaft (308); a displacement encoder (307) is further on the linkage driving shaft (308).

7. The winding tester for composite wire rod-type specimens of claim 1, wherein the two lateral plates (201) of the shield (2) are configured with a bi-layer configuration with an inner layer (202) of metal punching screen and an outer layer (203) of organic glass plate.

8. The winding tester for composite wire rod-type specimens of claim 7, wherein the top plate (204) of the shield (2) is a removable metal plate.

9. The winding tester for composite wire rod-type specimens of claim 8, wherein at the front lateral of the shield (2) two visual gates (4), which are configured with material of bi-layer colorless toughened glass with mutually receiving by seal glue therebetween, are disposed.

10. The winding tester for composite wire rod-type specimens as any one of claim 1-9, wherein a visual monitoring system is further arranged on the shield (2).

* * * * *